US005792828A

United States Patent [19]
Quinn

[11] Patent Number: 5,792,828
[45] Date of Patent: Aug. 11, 1998

[54] DRY BLENDING OF ACRYLAMIDOALKANESULFONIC ACID MONOMER WITH BASIC COMPOUNDS

[75] Inventor: Robert E. Quinn, Cleveland, Ohio

[73] Assignee: The Lubrizol Corporation, Wickliffe, Ohio

[21] Appl. No.: 746,401

[22] Filed: Nov. 8, 1996

[51] Int. Cl.⁶ .................................................. C08G 75/00
[52] U.S. Cl. ..................... 528/373; 528/360; 528/363; 528/364; 525/328.5; 525/329.4; 252/32; 252/33
[58] Field of Search ........................ 528/360, 373, 528/363, 364; 252/32, 33; 525/328.5, 329.4

[56] References Cited

U.S. PATENT DOCUMENTS

| 3,332,904 | 7/1967 | Combe . |
|---|---|---|
| 3,506,707 | 4/1970 | Miller . |
| 3,544,597 | 12/1970 | Killam . |
| 3,556,803 | 1/1971 | Ehrreich et al. . |
| 3,692,673 | 9/1972 | Hoke . |
| 4,176,081 | 11/1979 | Surbey et al. . |
| 4,701,283 | 10/1987 | Itoh et al. . |

FOREIGN PATENT DOCUMENTS

| 853443 | 3/1995 | Germany . |
|---|---|---|
| 6-192201 | 7/1994 | Japan . |
| 7-101932 | 4/1995 | Japan . |
| 7316125 | 12/1995 | Japan . |

*Primary Examiner*—Duc Truong
*Attorney, Agent, or Firm*—David M. Shold

[57] ABSTRACT

A salt of an acrylamidoalkanesulfonic acid can be conveniently prepared by preparing a solid mixture of a normally solid acrylamidoalkanesulfonic acid and a basic compound which is reactive with the acrylamidoalkanesulfonic acid to form the salt. The solid mixture is combined with a solvent in which neutralization of the acrylamidoalkanesulfonic acid occurs.

22 Claims, No Drawings

DRY BLENDING OF ACRYLAMIDOALKANESULFONIC ACID MONOMER WITH BASIC COMPOUNDS

BACKGROUND OF THE INVENTION

The present invention relates to solid mixtures of sulfonic acid with basic compounds and the use of such blends in the preparation of salts.

Acrylamidoalkanesulfonic acids are commercially important monomers, useful in the preparation of copolymers suitable for number of applications, including ion exchange resins, polymers useful for increasing the affinity of acrylonitrile copolymers for basic dyes, copolymers useful as resins and films, as well as in the preparation of flocculants, dispersants, adhesives, and thickeners. For many such uses the salt form of the acid is desirable. It would be convenient to provide a form of acrylamidoalkanesulfonic acid which is readily handleable and which, upon solution, forms the desired salt in situ. The salt can then be polymerized or otherwise processed into the desired end product.

U.S. Pat. No. 4,176,081, Surbey et al., Nov. 27, 1979, discloses preparation of solutions of acrylamidoalkanesulfonic acid salts in organic liquids, by reacting the acid with a metal salt of a weak acid in the organic liquid in the presence of a free radical polymerization inhibitor. Sodium carbonate is used in the examples.

U.S. Pat. No. 3,506,707, Miller, Apr. 14, 1970, discloses acrylamidoalkane sulfonic acids prepared by reacting an olefinic compound containing at least one allylic hydrogen atom with an acyl hydrogen sulfate, and reacting the intermediate with water and an acrylonitrile below the temperature of polymerization.

U.S. Pat. No. 3,332,904, Combe, Jul. 25, 1967, discloses water-soluble interpolymers of acrylamidoalkylsulfonates. In the examples, the sulfonic acid is reacted with sodium acetate.

U.S. Pat. No. 3,692,673, Hoke, Sep. 19, 1972, discloses polymers of acrylamide sulfonic acids and their salts. The sulfonic acid monomer is converted to its metal salt prior to polymerization by means of a suitable alkaline reagent.

U.S. Pat. No. 4,701,283, Itoh et al., Oct. 20, 1987, discloses a process for preparing amidoalkanesulfonic acids. A sulfate of the amidoalkanesulfonic acid salt can be neutralized in a polar organic solvent by adding thereto a predetermined amount of a basic substance as such or as a solution or suspension in water or a polar organic solvent.

U.S. Pat. No. 3,556,803, Ehrreich et al., Jan. 19, 1971, discloses a solid material formed of an at least slightly water soluble polymeric acid and a carbonate. When the solid material is placed in a container of water, the acid and carbonate react to evolve carbon dioxide and a substantially water insoluble salt. In an example, a polyacrylic acid is dispersed with calcium carbonate in toluene, the toluene is evaporated, and a wafer is pressed.

SUMMARY OF THE INVENTION

The present invention provides a solid mixture comprising (a) a normally solid acrylamidoalkanesulfonic acid; and (b) a normally solid basic compound which is reactive with the acrylamidoalkanesulfonic acid in solution to form the salt thereof, said mixture being substantially free from solvent in which said salt formation occurs.

The present invention further provides a method for preparing a salt of an acrylamidoalkanesulfonic acid, comprising combining the aforementioned solid mixture with a solvent in which neutralization of the acrylamidoalkanesulfonic acid occurs.

DETAILED DESCRIPTION OF THE INVENTION

The first component of the solid mixture of the present invention is a normally solid acrylamidoalkanesulfonic acid. The term "normally solid" indicates that the material in question is a solid under normal conditions of storage, handling, mixing (exclusive of high temperature mixing), and compacting. Thus the solid will generally have a melting point above room temperature, preferably above 50° C., and more preferably above 60° C.

Acrylamidoalkanesulfonic acids are materials represented by the formula

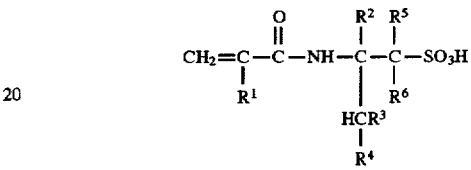

wherein, in the preferred embodiments, $R^1$ is hydrogen or a lower hydrocarbyl or alkyl radical and each of $R^2$, $R^4$, $R^5$, and $R^6$ is independently hydrogen or an alkyl or hydrocarbyl radical, and $R^3$ is hydrogen, an alkyl or hydrocarbyl radical, or an $SO_3H$ group. The term "lower" as used in this context designates radicals containing up to 7 carbon atoms. The term "acrylamidoalkanesulfonic acid" thus includes materials made from methacrylic acid (where $R^1$ is methyl), ethacrylic acid, and the like, and not just acrylic acid. Preferably the alkyl group $R^1$ has 6 or fewer carbon atoms, more preferably 3 or fewer carbon atoms. More preferably yet $R^1$ is methyl, and most preferably it is hydrogen.

Preferably each of $R^2$, $R^3$, $R^4$, $R^5$, and $R^6$ is hydrogen or a lower alkyl radical. In a preferred embodiment, $R^2$ is methyl, while $R^1$, $R^3$, $R^4$, $R^5$, and $R^6$ are hydrogen. Such a material is 2-acrylamido-2-methylpropane sulfonic acid, represented by the formula

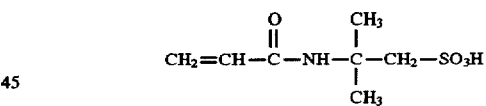

(The commercial grade material is believed to include a fraction containing two sulfonic acid groups, that is, where $R^3$ is an $SO_3H$ group.) This material is commercially available from The Lubrizol Corporation as AMPS® monomer, and from Toa Gosei under the trade name "ATBS." Other useful materials of this class include 2-acrylamidoethanesulfonic acid, 2-acrylamidopropanesulfonic acid, 2-methacrylamidopropanesulfonic acid, and 2-methacrylamido-2-methylpropanesulfonic acid. Such materials are disclosed, for instance, in U.S. Pat. No. 3,544,597.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl)

substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

The second component of the solid mixture of the present invention is a basic compound which is reactive with the acrylamidoalkanesulfonic acid in solution to form the salt thereof. It is preferred that the basic compound comprises an anion which forms a volatile compound upon acidification. The basic compounds thus include conventional bases such as hydroxides or oxides (producing water upon acidification), as well as basic salts such as acetates (producing acetic acid), other alkanoates, and carbonates and bicarbonates (producing carbon dioxide). Volatile compounds may be defined, for the purpose of the present invention, as those which exhibit a significant vapor pressure at room temperature and which can be removed from a solution, if desired, by evaporation, optionally with heating or under vacuum. Volatile materials generally have a boiling point at atmospheric pressure of 130° C. or less, preferably 100° C. or less, more preferably 70° C. or less. Most preferably they are gases at room temperature.

The basic compound will generally be a metal, ammonium ($NH_4^+$), or amine ($NR_4^+$) compound, such as an alkali metal, alkaline earth metal, ammonium, or amine salt. Preferably the cation will be lithium, sodium, potassium, calcium, or magnesium, so that basic compound will be is a lithium, sodium, potassium, calcium, or magnesium compound.

Among the highly preferred examples of the basic compounds are lithium carbonate, lithium hydroxide, sodium carbonate, sodium bicarbonate, potassium carbonate, potassium bicarbonate, calcium carbonate, calcium hydroxide, magnesium carbonate, and magnesium hydroxide. Particularly preferred is sodium carbonate, although any appropriate metal compound may be employed to provide the desired metal salt of the acrylamidoalkanesulfonate.

All of the basic compounds employed in the present invention are well known and commercially available materials. They may be used singly or in combination, and they may be used in chemically pure or in commercial grade form, depending on the desired end use and purity of the acrylamidoalkanesulfonic acid salt. They should preferably be used in a substantially anhydrous form, that is, free from substantial amounts of adsorbed or absorbed water or other protic materials that could lead to proton transfer and neutralization reaction when they are mixed with the acrylamidoalkane sulfonic acid. They should likewise be sufficiently free from liquids that the resulting mixture can be characterized as a solid, rather than a slurry or liquid. Preferably the mixture will be sensibly dry and will be readily handleable in solid form. Hygroscopic materials should preferably be suitably protected to minimize absorption of atmospheric water.

The relative amounts of the first two components of the mixture are not particularly critical, although normally they will be used in approximately equivalent amounts in order to form the fully neutralized salt. It is also possible that less than an equivalent amount of the basic compound can be used if it is desired that the acrylamidoalkanesulfonic acid be incompletely neutralized, and greater than an equivalent amount can likewise be used if desired. Most commonly the equivalent ratio of acid to base will be 1:0.8 or 1:0.9 up to 1:2 or 1:1.5. More preferably the ratio will be 1:1 to 1:1.1.

The mixture will be substantially free from solvent in which salt formation by reaction of the two major components can occur. Such solvents are described in greater detail below. To the extent that any of the components of the blend are hygroscopic, the composition will preferably be protected from atmospheric moisture.

The mixture can contain other ingredients in amounts suitable for their known functions. For instance, the mixture can contain solid flow control agents such as fumed silica, defoamers and antifoam agents, buffers for control of pH, inhibitors for control of free radicals, or chelating agents for control of contamination by iron or other metals.

The solid mixture of the present invention is prepared by any convenient means for admixing the components. Preferably the admixing is conducted by dry blending, which can be accomplished by manual blending, batch blending, or in-line dry blending. The components to be blended can be provided in powder, granular, pellet, or briquette form, thus the components can be pregranulated, if desired, before the mixing process.

Alternatively, the solid mixture can be prepared by admixing in an inert liquid medium, followed by separation of the solids from the medium. The inert medium will be one wherein no significant neutralization of the acid will occur; preferably it will be a medium in which neither component is soluble. The reactive liquid media set forth below are generally unsuitable for this use. Examples of inert media include aliphatic and aromatic hydrocarbons such as hexanes, octanes, kerosene, Stoddard solvent, mineral spirits, benzene, toluene, and xylenes, ethers, liquid carbon dioxide, and acrylonitrile. Separation of solids from the inert medium can be by any conventional means, including filtration, centrifugation, decantation, evaporation of the medium, spray drying, or freeze drying.

The solid mixture of the present invention can be subjected to compaction. This compaction can be as a separate step after the mixing step, or it can be conducted as a part of the mixing operation. Compaction encompasses a variety of processing steps which are known to those skilled in the art. These processes include pressing, granulation, pelletizing, and milling. The result of the compaction process is a product which has a higher bulk density and is in a denser, more compact form, often with reduced loose powder content. The compacted product may also have reduced surface area and can exhibit improved flow and handling properties.

The composition described in detail above can be used to prepare a salt of an acrylamidoalkanesulfonic acid. The salt formation involves combining the solid mixture, described in detail above, with a solvent in which neutralization of the acrylamidoalkanesulfonic acid occurs. This combining or mixing can be by any convenient means. The solid mixture can be added to the solvent, or the solvent can be added to the solid mixture. It is generally desirable to assist solution and neutralization by stirring or other means of mechanical mixing, which can be conducted in a stirred tank or other apparatus such as extruders, mills, or eductors. If desired, the mixture can be heated to facilitate solution; thus the reaction can be conducted from about room temperature or below up to the temperature of the boiling point of the solvent. In many cases the neutralization reaction is exothermic, so that no external heating is required.

The solvent employed is one in which neutralization of the acrylamidoalkanesulfonic acid by the basic material occurs. The solvent will, thus, be a liquid in which migration of the cation from the basic material to the acid will occur. Preferably, therefore, at least one, and preferably both of the acid and basic material exhibit at least a modest degree of solubility in the solvent, and preferably both such materials are substantially soluble in the solvent under ambient conditions.

In most instances, the solvent is a protic solvent or a polar aprotic solvent. Selection of the solvent can be based in part on the requirements for further reaction or handling of the resulting neutralization product. Thus if the acrylamidoalkanesulfonic acid salt will be used in an aqueous-medium polymerization, water would be a logical selection for the solvent. Protic solvents include water (which is preferred), alcohols such as methanol, ethanol, propanols, butanols, pentanols, hexanols, octanols, and mixtures thereof, including polyols such as diols (e.g., ethylene glycol, propylene glycol) and alcohols with more than two hydroxy groups (e.g., glycerol), carboxylic acids such as formic acid, acetic acid, propionic acid, and acrylic acid, amines such as trimethanolamine, and N-unsubstituted amides such as dimethylformamide and dimethyl acetamide. The protic solvent should not be a strong acid or a strong base which would compete with or interfere with the desired neutralization reaction of the acrylamidoalkanesulfonic acid by the basic compound from the solid mixture. Thus any acid employed should have a $pK_a$ greater than that of (i.e., be a weaker acid than) the acrylamidoalkanesulfonic acid. Likewise, if a basic material is employed as the solvent, it should be a weaker base than the basic compound from the solid mixture.

Polar aprotic solvents include N-substituted amides such as, most commonly, dimethylformamide, dimethylacetamide, and dimethylsulfoxide.

If a nonaqueous solvent is used, and especially if a polar aprotic solvent is used, it may be desirable to include in the solvent medium at least a catalytic amount of a protic material, preferably water, in order to promote the neutralization reaction. This is not always required, however, since the neutralization reaction itself will normally produce water as a byproduct, so that the neutralization can proceed, although perhaps after an initial period of slow reactivity. The amount of water or other protic material would preferably be at least 0.5 percent by weight, preferably at least 2 percent.

The amount of solvent employed is not critical and will depend largely on the concentration of the resulting salt which is desired. Typically the solid:solvent ratio will be 0.1:99.9 to 70:30 or 60:40, preferably 1:99 to 50:50, or 10:90 to 40:60.

After the neutralization reaction is complete, a byproduct will normally be the neutralization product of the anion from the basic material. In some cases it may be acceptable or desirable for this neutralization product to remain in solution along with the salt of the acrylamidoalkanesulfonic acid. If the neutralization product is water, it can conveniently remain in an aqueous system. Sometimes, however, it will be desirable that this byproduct be removed. Removal can be accomplished by any known chemical or physical methods.

In preferred embodiments of the present invention, the byproduct is a volatile material which can be removed by evaporation, distillation, or other similar methods. In certain preferred instances, where the basic material is, for instance, a carbonate or bicarbonate, the neutralization byproduct will be a gas such as carbon dioxide, which spontaneously evolves from the system. Appropriate means for exhausting or venting such gaseous byproducts should be provided.

The solid mixtures of the present invention, particularly when in a granulated form, are low dust, free flowing materials, exhibiting increased bulk density, improved package stability compared to salt solutions, improved solution color, improved pH stability, reduced corrosiveness, rapid product dissolution, controlled temperature upon neutralization (especially in instances when a gas such as $CO_2$ is evolved), improved ease of neutralization, including reduced possibility of contamination or other impurity formation, the opportunity for multiple salt formation in the same equipment, reduced nitrogen purge requirements, reduced water contamination, including improved pH of waste water, and improved odor.

It is known that some of the materials described above may interact upon mixing, so that the components of the final formulation may be different from those that are initially added. For instance, metal ions can migrate to acidic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

Example 1

(a) A 3.8 L (1 gallon) wide-mouth plastic jar is charged with 414 g (2 moles) 2-acrylamido-2-methylpropanesulfonic acid and 111 g (1.1 moles) sodium carbonate. The jar is closed and shaken until the contents are uniformly mixed; any apparent lumps are broken up using a spatula.

A 5-g aliquot of the composite powder is added to a 28.6 mm (1⅛ inch) stainless steel mold and compressed under 89 kN (20,000 pounds) force to form a pellet.

(b) The pellet is removed and dissolved in 95 g distilled water. A mildly exothermic reaction and generation of gas is observed upon dissolution.

Example 2

Example 1(a) is substantially repeated except that the amount of sodium carbonate used is 106 g (1.05 moles).

Example 3

Example 1(a) is substantially repeated except that the amount of sodium carbonate used is 101 g (1.0 moles).

Example 4

A "V-Blender" blending device is charged with 12.5 kg (27.6 pounds, 60.4 moles) 2-acrylamido-2-methylpropanesulfonic acid and 3.36 kg (7.4 pounds, 31.7 moles) sodium carbonate. The composition is mixed, then compacted and granulated on a roll compactor at 4 revolutions per minute and 450–690 kPa (65–100 psig) at 46°–60° C. (114°–140° F.) and sized.

Example 5

Example 1(a) is substantially repeated except that the sodium carbonate is replaced by an equivalent amount of ammonium carbonate. (In an example in which this was carried out, the solid blend was found to be less stable to storage in packaging than was the blend of claim 1.)

Example 6

Example 2 is substantially repeated except that in place of the sodium carbonate there is used an equivalent amount of lithium hydroxide.

Example 7

Example 2 is substantially repeated except that in place of the sodium carbonate there is used an equivalent amount of calcium hydroxide.

Example 8

Example 2 is substantially repeated except that in place of the sodium carbonate there is used an equivalent amount of sodium bicarbonate.

Example 9

Example 2 is substantially repeated except that in place of the 2-acrylamido-2-methylpropanesulfonic acid there is used an equivalent amount of 2-methacrylamidopropanesulfonic acid.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. It is to be understood that the amount, range, and ratio limits set forth herein may be combined. As used herein, the expression "consisting essentially of" permits the inclusion of substances which do not materially affect the basic and novel characteristics of the composition under consideration.

What is claimed is:

1. A solid mixture comprising (a) a normally solid acrylamidoalkanesulfonic acid; and (b) a normally solid basic compound which is capable of reacting with the acrylamidoalkanesulfonic acid in solution to form the salt thereof;

said mixture being substantially free from solvent in which said salt formation occurs;

wherein components (a) and (b) are not in solution and are not reacted with each other.

2. The mixture of claim 1 wherein the acrylamidoalkanesulfonic acid is a compound represented by the formula

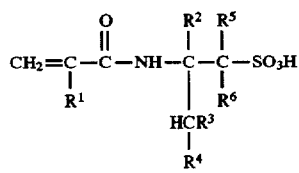

wherein $R^1$ is hydrogen or a lower alkyl radical and each of $R^2$, $R^4$, $R^5$, and $R^6$ is independently hydrogen or an alkyl radical, and $R^3$ is hydrogen, an alkyl radical, or an $SO_3H$ group.

3. The mixture of claim 1 wherein the acrylamidoalkanesulfonic acid is a compound represented by the formula

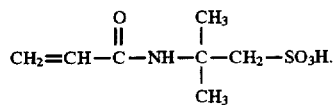

4. The mixture of claim 1 wherein the basic compound comprises an anion which forms a volatile compound upon acidification.

5. The mixture of claim 1 wherein the basic compound is a carbonate, bicarbonate, oxide, hydroxide, or acetate.

6. The mixture of claim 1 wherein the basic compound is a carbonate or a bicarbonate.

7. The mixture of claim 1 wherein the basic compound is an alkali metal, alkaline earth metal, ammonium, or amine compound.

8. The mixture of claim 1 wherein the basic compound is a lithium, sodium, potassium, calcium, or magnesium compound.

9. The composition of claim 1 wherein the basic compound is sodium carbonate.

10. The composition of claim 1 wherein components (a) and (b) are present in an equivalent ratio of about 1:0.8 to about 1:2.

11. The composition of claim 1 wherein components (a) and (b) are present in an equivalent ratio of about 1:1 to about 1:1.1.

12. A composition prepared by admixing the components of claim 1.

13. The composition of claim 12 wherein the admixing is conducted by dry blending.

14. The composition of claim 13 wherein the admixing is conducted by in-line static mixing.

15. The composition of claim 12 wherein the admixing is conducted in an inert liquid medium, followed by removal of the medium.

16. The composition of claim 15 wherein the inert medium is acrylonitrile.

17. The composition of claim 13 wherein the composition is subjected to compaction.

18. A method for preparing a salt of an acrylamidoalkanesulfonic acid, comprising combining the solid mixture of claim 1 with a solvent in which neutralization of the acrylamidoalkanesulfonic acid occurs.

19. The method of claim 18 wherein the solvent is a protic solvent or a polar aprotic solvent.

20. The method of claim 19 wherein the polar aprotic solvent contains at least a catalytic amount of a protic solvent.

21. The method of claim 19 wherein the solvent is a nonaqueous solvent containing at least a catalytic amount of water.

22. The method of claim 19 wherein the solvent is selected from the group consisting of water, alcohols, polyols, carboxylic acids, and amides.

* * * * *